(12) United States Patent
Breidenbach et al.

(10) Patent No.: US 11,896,972 B2
(45) Date of Patent: Feb. 13, 2024

(54) DEVICE HAVING A FIRST CHAMBER FOR RECEIVING A BODY FLUID

(71) Applicant: ORTHOGEN AG, Düsseldorf (DE)

(72) Inventors: Nina Breidenbach, Düsseldorf (DE); Julio Reinecke, Cologne (DE); Julien Troillet, Markkleeberg (DE); Peter Wehling, Düsseldorf (DE); Julia Heindirk, Korschenbroich (DE)

(73) Assignee: ORTHOGEN AG, Dusseldorf (DE)

( * ) Notice: Subject to any disclaimer, the term of this patent is extended or adjusted under 35 U.S.C. 154(b) by 554 days.

(21) Appl. No.: 16/652,620

(22) PCT Filed: Oct. 10, 2018

(86) PCT No.: PCT/EP2018/077574
§ 371 (c)(1),
(2) Date: Mar. 31, 2020

(87) PCT Pub. No.: WO2019/072903
PCT Pub. Date: Apr. 18, 2019

(65) Prior Publication Data
US 2020/0238274 A1    Jul. 30, 2020

(30) Foreign Application Priority Data
Oct. 11, 2017    (EP) .................................... 17195982

(51) Int. Cl.
*B01L 3/00*    (2006.01)
(52) U.S. Cl.
CPC ....... *B01L 3/5021* (2013.01); *B01L 2200/026* (2013.01); *B01L 2200/0621* (2013.01);
(Continued)

(58) Field of Classification Search
CPC ............. B01L 3/5021; B01L 2200/026; B01L 2200/0621; B01L 2300/044;
(Continued)

(56) References Cited

U.S. PATENT DOCUMENTS 3,076,305 A     2/1963  Meisser
3,706,305 A  *  12/1972  Berger ............. A61B 5/150732
                                                            422/550
(Continued)

FOREIGN PATENT DOCUMENTS

CN      102264410 A      11/2011
CN      103501832 A       1/2014
(Continued)

OTHER PUBLICATIONS

International Search Report for PCT/EP2018/077574, dated Nov. 27, 2018 (PCT/ISA/210).
(Continued)

*Primary Examiner* — Matthew D Krcha
*Assistant Examiner* — Jacqueline Brazin
(74) *Attorney, Agent, or Firm* — Sughrue Mion, PLLC

(57) ABSTRACT

The invention relates to an apparatus for receiving a body fluid, wherein the apparatus comprises a first chamber with a displaceable wall and a second chamber of a constant effective size, said second chamber being movable with respect to the displaceable wall, wherein the apparatus is designed to connect the first chamber and the second chamber during a longitudinally axial movement of the second chamber with respect to the displaceable wall and to transfer body fluid from the first chamber to the second chamber during a movement of the second chamber together with the displaceable wall.

11 Claims, 3 Drawing Sheets

Figure 1:
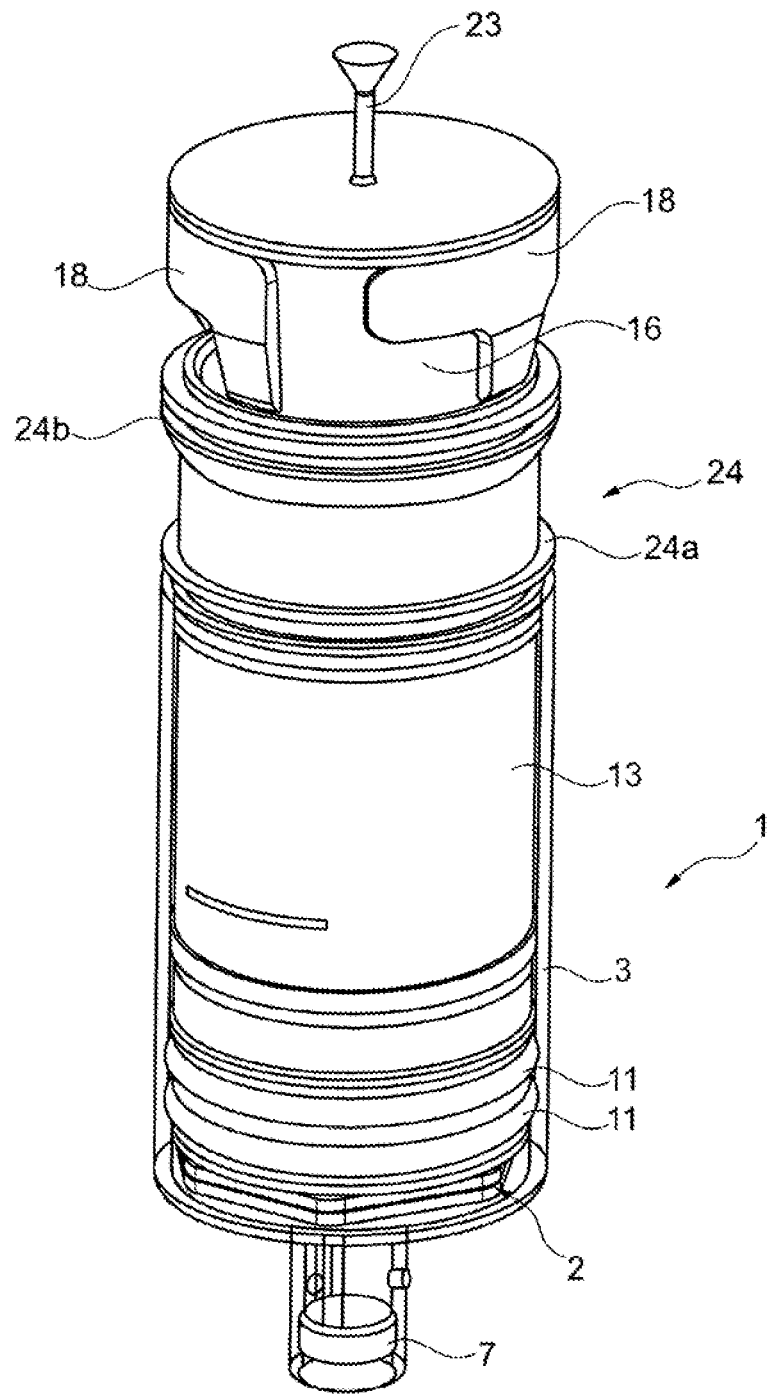

(52) U.S. Cl.
CPC . *B01L 2300/044* (2013.01); *B01L 2300/0672* (2013.01); *B01L 2300/087* (2013.01); *B01L 2300/0832* (2013.01); *B01L 2400/0409* (2013.01)

(58) Field of Classification Search
CPC ..... B01L 2300/0672; B01L 2300/0832; B01L 2300/087; B01L 2400/0409; B01L 2300/045; B01L 2400/0478; B01L 3/502; A61M 1/3693; A61M 1/029
USPC ........................................................ 422/548
See application file for complete search history.

(56) References Cited

U.S. PATENT DOCUMENTS

| | | | |
|---|---|---|---|
| 4,209,488 | A | 6/1980 | Breno |
| 4,644,807 | A | 2/1987 | Mar |
| 4,828,716 | A | 5/1989 | McEwen et al. |
| 5,360,011 | A | 11/1994 | McCallister |
| 5,603,845 | A * | 2/1997 | Holm ................. B04B 7/00 494/7 |
| 6,398,972 | B1 | 6/2002 | Blasetti et al. |
| 2003/0205538 | A1 | 11/2003 | Dorian et al. |
| 2008/0166421 | A1 | 7/2008 | Buhr et al. |
| 2009/0286309 | A1 | 11/2009 | Roderfeld |

FOREIGN PATENT DOCUMENTS

| | | |
|---|---|---|
| CN | 104704106 A | 6/2015 |
| DE | 603 14 413 T2 | 2/2008 |
| EP | 2 123 289 A1 | 11/2009 |
| JP | 7-185393 A | 7/1995 |
| RU | 2 370 286 C2 | 10/2009 |
| RU | 2 591 658 C2 | 7/2016 |

OTHER PUBLICATIONS

Office Action, dated Sep. 27, 2022, issued by the Japanese Patent Office in Japanese Patent Application No. 2020-518475.
Office Action dated Jun. 22, 2022 issued by the Russian Patent Office in Russian Application No. 2020114945/14.
Office Action dated Jul. 28, 2022 issued by the Australian Patent Office in Australian Application No. 2018348719.
Office Action dated Jun. 6, 2022 issued by the Brazilian Patent Office in Brazilian Application No. BR112020006199-9.
Office Action dated May 16, 2023 in Russian Application No. 2020114945/14.
South Korean Office Action for Application No. 10-2020-7010997 dated Oct. 27, 2023; 10 pages total.
Office Action issued in Mexican Application No. MX/a/2020/003432 dated Oct. 30, 2023.

* cited by examiner

DEVICE HAVING A FIRST CHAMBER FOR RECEIVING A BODY FLUID

CROSS REFERENCE TO RELATED APPLICATIONS

This application is a National Stage of International Application No. PCT/EP2018/077574 filed Oct. 10, 2018, claiming priority based on European Patent Application No. 17195982.8, filed Oct. 11, 2017.

The present invention relates to an apparatus and a method for transferring body fluids as well as to a use.

Apparatuses for separating individual blood phases, for example, by using a centrifuge, or for producing and separating biologically active substances, such as, for example, autologous proteins, are known.

The document US 2008/0166421 A1 discloses a method for processing plasma, in which method a syringe-like apparatus is designed as a plunger component of an additional syringe-like apparatus. According to said document, two syringe-like apparatuses are "connected in series one after the other". Thus, two chambers are used, each of which has a displaceable wall. In this way a whole apparatus is made available that requires a skilled operator. The steps for handling parts that are to be operated or, more specifically, to be moved in relation to each other by the operator are complex. The automation of said steps is simply not possible.

The document U.S. Pat. No. 4,644,807 A discloses an apparatus for transferring samples of a liquid to be analyzed in a chromatographic column. Described is a sample holding vial, in which a plunger can be moved so as to be displaced by sliding. By moving the plunger, the liquid, present in the sample holding vial, can be compressed and rises in a column, while simultaneously displacing the air. A simple, especially sterile, processing of the liquid is not possible.

The document U.S. Pat. No. 4,209,488 A discloses an apparatus for the processing of samples. Two separate chambers are provided.

The document EP 2 123 289 A1 discloses an apparatus for producing a biologically active substance. Described is a wing-free and pistonless container, to which blood constituents can be transferred after the blood has been collected and/or conditioned. The container contains beads as the shearing bodies that are used to expose the blood constituents to a stressful situation, which can lead to the formation of a biologically active substance. After the biologically active substance has been produced, the container can be transferred to a centrifuge; and the blood phases are separated according to their density. In addition to the container, another container for collecting or conditioning the blood as well as for transferring the blood between the separate container and the container are necessary. This situation leads to a plurality of process steps that an operator has to carry out, while at the same time there is a risk of contamination.

The document DE 603 14 413 T2 describes a method and an apparatus for isolating platelets of blood, the blood being supplied to a separating apparatus for blood platelets by means of an external blood collecting apparatus in a preceding step. The transfer of the blood to various containers implies the risk of contamination and requires several process steps.

The document U.S. Pat. No. 4,828,716 A discloses an apparatus and a method for separating phases of blood. The apparatus comprises a tubular chamber, which has been evacuated and in which a negative pressure is present. By using a double-ended needle, it is possible to fill the blood directly into said tubular chamber by means of the negative pressure while the blood is being collected. The chamber, which has been filled with blood, can be rotated about its longitudinal axis, in order to separate the individual phases of the blood from one another, so that the phases are concentric with one another in the chamber. In order to separate the phases even more from one another, the chamber is rotated about its longitudinal axis; and an operator pushes a separating element into the chamber with a rod, so that the centrally arranged phase is shifted upwards in the chamber, while an equalization of the pressure is implemented at the same time. The steps of the process are complex and pose the risk of contamination.

The document U.S. Pat. No. 8,052,969 B2 describes a method for producing platelet-rich blood plasma by using a two-chamber syringe. In the case of the two-chamber syringe the plunger of a first syringe is designed again as a (second) syringe. After the first syringe has been filled with blood, the two-chamber syringe can be subjected to a centrifugation process, where the individual components are separated from one another as a function of their density. In a step downstream of the centrifugation run, the top, platelet-rich plasma layer can be separated from the bottom layer by means of the second syringe. At the same time the plasma is drawn into the cavity of the second syringe. Then the second syringe can be separated from the first syringe. The process steps to be carried out require an experienced operator, while at the same time contamination cannot be ruled out.

The document U.S. Pat. No. 3,706,305 A describes an apparatus that is a combination of a vacuum syringe for collecting blood, a centrifuge container and a specimen cup. Vacuum chambers of a constant effective size are combined with one another. The result is a relatively long structure, which, in addition, provides a handling option that is relatively inflexible. After the blood has been collected, the blood is passed into a centrifuging chamber. Then the individual blood phases can be separated from one another by centrifuging. In order to separate the serum phase from the rest of the blood constituents in a subsequent step and to transfer said blood phase to the specimen cup, which is under vacuum, said specimen cup has to be manually connected to the inside of the centrifuging chamber by means of a transfer needle. In so doing, atmospheric air flows into the centrifuging chamber for purposes of balancing the pressure. The process steps to be carried out require a skilled operator, while at the same time contamination of the blood components cannot be ruled out.

The document U.S. Pat. No. 6,398,972 B1 discloses a method for producing a platelet-rich plasma; and said method uses an apparatus, in which two integrally formed containers are present. The two containers are arranged next to one another and are continuously connected to one another by means of a flow channel. An operator is required for the transfer of the phases or a treatment in the centrifuge that is different from the centrifugation process to separate the phases.

Against this background, it is an object of the present invention to provide an apparatus and a method as well as a use in such a way that said apparatus and/or method improves and/or improve the transfer of a phase of a body fluid, where in this case an improvement can be considered to consist of providing the smallest possible number of process steps for the operator, improving the handling and/or carrying out a transfer of the body fluid in as sterile a manner as possible.

The object is achieved by means of the subject matter of the independent patent claims. Advantageous embodiments are the subject matter of the dependent patent claims and shall become apparent from the following description.

In one aspect the invention relates to an apparatus for receiving a body fluid, wherein the apparatus comprises a first chamber, which has a displaceable wall, and a second chamber, in particular, of a constant effective size, said second chamber being movable with respect to the displaceable wall, wherein the apparatus is designed to connect the first chamber and the second chamber during a longitudinally axial movement of the second chamber with respect to the displaceable wall, and to transfer body fluid from the first chamber to the second chamber during a movement of the second chamber together with the displaceable wall. In this way it is possible to make available an apparatus that is simple in design and is easy to handle; and with said apparatus a longitudinally axial movement can cause the transfer.

In a second aspect of the invention, in which the structural configuration of the apparatus, according to the first aspect, can be used, but another configuration is also possible, an apparatus comprising a first chamber for receiving a body fluid and a second chamber is made available. During the centrifugation process for separating the phases of the body fluid, the first chamber and the second chamber can be connected; and during the centrifugation process the body fluid can be transferred from the first chamber to the second chamber by means of the centrifugal force. The number of process steps, to be performed by an operator, is reduced. In accordance with the second aspect, it can be provided that the first chamber does not have a displaceable wall, but rather is designed as a container that has a substantially constant volume and a negative pressure.

In a third aspect an apparatus is made available that can have a structural configuration like the apparatus in accordance with the first aspect, but a different structural configuration is also possible, where in this case the apparatus comprises a first chamber for receiving a body fluid and a second chamber. The apparatus is designed (in particular, after a centrifugation run and after separation of the phases of the body fluid) to carry out a longitudinally displaceable movement, during which the apparatus is compressed; and the body fluid is transferred from the first chamber to the second chamber. In this way it is possible to make available an apparatus that is simple in design and is easy to handle.

In one aspect the invention is based on the basic idea of utilizing the acting forces during a centrifugation run in order to make possible a movement that is induced by the forces, so that during said movement the chambers can be connected to one another; and a transfer or, more specifically, the passing of the body fluid at least partially between the chambers during the centrifugation process is made possible due to the acting forces. The inventors have recognized that for the separation or, more specifically, partitioning of the individual phases or, more specifically, components of the body fluids, forces are generated that, in addition to the separation or, more specifically, partitioning of the individual phases, can be used to transfer a phase from one chamber to another chamber.

The following description applies to every aspect of the invention and can be combined with any of the aspects that are mentioned. In particular, the first aspect can also be combined with the second aspect as well as the first aspect and the third aspect. It can also be provided that the second aspect and the third aspect can be combined with one another, for example, in order to make possible an at least partial transfer during a centrifugation run and an additional or final transfer of the body fluid after the centrifugation run.

An apparatus can be provided that makes possible a collection, a modification, a separation, an isolation and/or storage of the body fluid components, in particular, the phases that can be separated from one another, by a centrifugation process, by means of a single apparatus. As a result, it is possible to ensure that the handling of the body fluids will be as sterile as possible. The operator no longer has to carry out steps that require a lot of practice and/or experience.

In one aspect the invention makes available an apparatus comprising a first chamber for receiving a body fluid and a second chamber. During centrifugation for the separation of phases of the body fluid, the first chamber and the second chamber are connected; and the body fluid is transferred at least partially from the first chamber to the second chamber during the centrifugation process by means of the forces acting in said process.

The term "body fluid" for the purpose of the patent specification includes a fluid of the human or animal body. The term includes primarily a liquid, where gaseous or solid fractions shall not be excluded. The term body fluid includes, in particular, saliva, lymph fluid, urine, bone marrow and preferably blood. The term "phase" or "component" of the body fluid includes fractions that can be separated from one another by means of a centrifugation process.

The term "chamber" for the purpose of the patent specification includes a cavity that can receive the body fluid and/or individual or several phases of the body fluid. The walls of the cavity may be designed so as to be preferably rigid. In particular, side walls of the chamber, i.e., the walls that extend along the longitudinal axis of the chamber, may be designed so as to be rigid. Depending on the embodiment, the effective size of the cavity can be constant (in particular, the second chamber) or variable (in particular, the first chamber), wherein the cavity can have a maximum size; and by moving a wall that extends, in particular, in a direction transverse to the longitudinal axis of the chamber, the size can be reduced or increased, for example, in order to push the fluid, contained therein, out of the chamber (in particular, the first chamber) or to draw it into the chamber (in particular, the first chamber). In the context of the present description, one chamber can be closed to the environment, wherein one chamber can be opened, in particular, after forming a sterile connection to the human or animal body, in order to receive or discharge the body fluid. In a preferred embodiment one of the two chambers can be removed from the apparatus. One of the chambers can be designed and arranged to be separated from the apparatus, so that the contents of the chamber can remain sterile in the chamber. The chambers can be designed in such a way that they can be separated from one another, and at least one chamber can remain closed or can be closed after separating. In particular, the chamber to be removed may be closed in an initial state or delivery state of the apparatus in such a way that said chamber is sterile. As an alternative or in addition, the other chamber is also closed in a sterile manner in this state. The chambers can form closed units in this state. One possible connection or rather the connecting elements, which allow the chambers to be connected, may be present in a sterile state, in particular, in an intermediate space between the chambers.

A chamber of constant effective size is a chamber, in which, in particular, the total volume that can be filled into the chamber remains the same or constant. The walls of the chamber of a constant effective size can be designed, in particular, as non-displaceable with respect to one another. In this respect the expression "chamber of constant effective size" is synonymous with "chamber with non-displaceable walls". In this case it is not ruled out that the walls of the chamber of a constant effective size may bulge or unfold, in particular, slightly. A chamber of constant effective size can also be a cavity, which is formed within a bellows-like construction, which is closed at one end, at least on one side, and said cavity can be filled with fluid and unfolds at least partially when it is being filled. Contact sections between the walls of the chamber of a constant effective size can be designed in a fixed manner. The walls can be permanently connected to one another. The chamber of a constant effective size has preferably a negative pressure.

Therefore, the apparatus can be arranged and designed to connect the first chamber and the second chamber during the centrifugation process, in order to separate the phases of the body fluid and to transfer the body fluid from the first chamber to the second chamber during this centrifugation process by means of the forces acting in said process. Similarly the first chamber, the second chamber and/or the elements of the apparatus described below can be configured, arranged or designed to provide or support this function.

In a preferred embodiment the two chambers of the apparatuses are (still) closed to the environment after receiving the body fluid in the first chamber. The apparatus can be delivered, in particular, in a sterile manner. Then the apparatus can be filled with body fluid in a sterile manner. Thereafter, the body fluid can be processed in the apparatus in a sterile manner. The sterility can be maintained or, more specifically, ensured throughout the entire process, in particular, the filling with blood, separation of the phases and transfer of a phase to the second chamber.

In particular, the first chamber can be configured or designed to collect body fluid, in particular, to collect blood, from the body. An opening or a connecting part, which is, in particular, reclosable, in particular, preferably automatically or rather independently, can be formed on the chamber, so that said opening or connecting part may be used by the apparatus to collect the body fluid. A septum is disposed preferably as a closure diaphragm at an opening of the first chamber in such a way that it can be reclosed, in particular, automatically or rather independently, after said chamber has been filled. For this purpose an opening with a septum can be arranged at the end of the first chamber, in particular, in an area that tapers off. The septum can be pierced, in order to fill the chamber and can be closed again after said chamber has been filled. The first chamber may have an end wall that can be moved in a displaceable manner on the side wall, in order to change the effective volume of the chamber. For example, the end of the first chamber can have a wall that can be moved by means of a plunger or a piston. The first chamber can have a "cylindrical section" or can be designed as such a cylindrical section; and said cylindrical section has a tubular section that can be enclosed by a lateral surface and two additional transverse surfaces, which can be in essence the sectional surfaces of the lateral surface. The opening with the septum can be formed on one of the transverse surfaces; and the other transverse surface can be the displaceable wall. The transverse surface with the opening can be formed in one piece with the side wall. The "cylindrical section" can be shown as a flat curve in a plane that is displaced by a predetermined distance along a straight line that is not contained in the aforementioned plane. The flat curve can be one or both of the aforementioned transverse surfaces at the start and end position of the displacement. The flat curve can be, in particular, a circle, an ellipse, a polygon or a combination of the aforementioned shapes. A vertical circular cylinder is particularly preferred as the cylindrical section for the purpose of the patent specification. In the case of a vertical circular cylinder, the displaceable wall has a substantially circular shape in cross section. The displaceable wall of the chamber can be present, in particular, as an end face of a plunger that can be displaced in a cylinder. The opening of the first chamber with the connecting part and/or the septum can be formed on the wall that lies opposite the displaceable wall as the transverse surface. It can be provided that the filling of the first chamber takes place by connecting a needle or cannula to the connecting part and by moving the displaceable wall of the first chamber, where in a particularly preferred embodiment the movement of the displaceable wall of the first chamber is limited by means of a stop element. The fill volume of the first chamber is preferably variable due to the displaceable wall. The fill volume of the first chamber can be 2 to 500 ml. It is possible that the fill volume of the first chamber is 5 to 500 ml, preferably 5 to 300 ml, furthermore, preferably 5 to 150 ml, more preferably 5 to 100 ml, preferably 5 to 50 ml, in particular, preferably 10 to 15 ml. It can also be provided that the first chamber has a vacuum and that it can be filled in accordance with the vacuum principle. In the case that the first chamber has a vacuum, there is a negative pressure in the first chamber, so that there is no need for a displaceable wall, in order to fill the first chamber.

A septum for the purpose of the patent specification comprises a normally self-closing closure, in particular, an elastomeric seal and/or closure diaphragm. However, it can also be provided that a septum for the purpose of the patent specification describes a closure that has to be actuated from the outside, so that the closure closes again, for example, a slide. For the purpose of the patent specification, a septum can also be a self-closing valve or a functionally identical structure of a closure that is designed in such a way that it automatically closes again after it has acted (for example, owing to pressure and/or a needle).

The term "plunger" for the purpose of the patent specification includes a movable component that together with a housing, in particular, the cylindrical section, can form a closed cavity (first chamber), the volume of which changes as a result of the movement of the plunger. The plunger can be reduced to a plate or disk (displaceable wall), which is moved in the cylindrical section.

In a preferred embodiment the apparatus has a barrier between the first chamber and the second chamber, where the barrier is closed preferably when the first chamber is being filled. The barrier can either prevent or allow fluid to flow through. The barrier can be arranged, in particular, on the first chamber and can close one or more openings of the first chamber, where said one or more openings allow a flow of at least one portion of the body fluid in the direction of the second chamber. The barrier and the one or more openings can be arranged on the wall of the chamber that is located opposite the opening for filling with a body fluid. The barrier can be part of the first chamber, so that the barrier can be handled and/or moved together with the first chamber.

In a preferred embodiment the body fluid can be modified within the first chamber after collection or rather after filling into the first chamber. For this purpose, additives can be provided in the first chamber. In the case of human or animal blood as the body fluid the typical additives are anticoagulants comprising EDTA, citrate, heparin and/or their derivatives. In a particularly preferred embodiment the inner surface area of the first chamber is enlarged, for example, by means of a method, which processes the inner surface area of the chamber and increases the roughness of the inner surface area. In a particularly preferred embodiment a substance, which changes and/or enlarges the inner surface area, is disposed in the first chamber and can have an inducing effect on the formation of autologous proteins. The surface-changing and/or surface-enlarging substances include glass powder, glass granulate, quartz powder, quartz sand, corundum, pellets, beads, sand and metals. The surface-changing and/or surface-enlarging substances also include organic compounds and polymers as well as biogenic or biological substances, such as, for example, cellulose, collagens, alginates, nucleic acids and other proteins or metabolites formed by cells. The surface-changing and/or surface-modifying substance can have an essentially solid, liquid or gel-like consistency. In an additional, particularly preferred embodiment additives, such as anticoagulants and/or a substance that changes and/or enlarges the inner surface area, are disposed in the first chamber. As an alternative, no additives are provided in the first chamber.

It is possible that a biologically active substance is present in the first chamber or that this biologically active substance is introduced into the first chamber with the body fluid already filled into said chamber. A biologically active substance is a substance that causes a change in the physiology or metabolism. Examples of a biologically active substance can be cortisone, genes or DNA or other aforementioned biogenic or biological substances.

In a preferred embodiment at least one opener is provided that is designed in such a way that it forms at least one partial fluid path arranged between the first chamber and the second chamber, in that the opener is an element and/or acts on an element that blocks or, more specifically, interrupts the partial fluid path. The opener can be, for example, a piercing means between the first and the second chamber, with said piercing means acting on a septum. Non-limiting examples of an opener include a valve, an element acting on a valve, a slide, an element acting on a slide, and/or a piercing means. It can be provided that the opener can be part of a closure; for example, the opener can be an actuating section of a slide.

The opener can open a closure of the second chamber, in particular, in that the second chamber is closed by means of a septum, which pierces an opener that is designed as a piercing means between the first chamber and the second chamber. The piercing means can be designed preferably as a single-ended or double-ended cannula, a single-ended or double-ended needle and/or a single edged or multi-edged blade. When the apparatus of the invention is introduced into a commercially available centrifuge, such as, for example, fixed angle or swing out centrifuges, the opener in a preferred embodiment can open a closure, which is attached to the second chamber, at an opening of the second chamber during a centrifugation run. The opener is preferably a piercing means; and the closure of the second chamber is a seal, which is arranged on one end and is directed towards the first chamber, for example, an elastomeric closure, of the second chamber; and, in particular, an opening of the second chamber can be closed again with said opener.

The term "elastomer" includes raw materials that deform elastically when subjected to tensile or compressive loads, but then return to their essentially original shape.

Furthermore, in particular, in addition to the opener and optionally a corresponding element, on which the opener acts, the barrier can be arranged between the first and the second chamber. The barrier can prevent the body fluid from flowing out of the first chamber in the direction of the second chamber. The barrier can be designed in such a way that there are in essence smooth walls that come into contact with the body fluid, so that openings and/or unevennesses, into which constituents of the body fluid can penetrate in certain states of the apparatus, can be reduced and/or avoided. The barrier can be designed in the form of a valve or can comprise such a valve. The barrier can prevent the body fluid from flowing in the direction of the second chamber in front of the opener and the closure of the second chamber. The barrier can be designed as a strictly physical barrier or, more specifically, as a blocking means, which either closes or opens. The barrier can be designed as a septum, which can be pierced by means of a needle or a similar piercing means, in order to allow a throughflow. A valve, as a barrier, can be designed as a check valve or "duckbill valve" or as an umbrella valve, in particular, arranged on the outside of a wall of the first chamber, where said wall lies opposite an opening that is provided for filling.

In a preferred embodiment a selection means can be arranged between the first and second chamber. The selection means can be designed preferably as a filter. A suitable filter can be a filter for selecting the size of the penetrating fluid. A pore size of a filter of essentially 100 μm, 90 μm, 20 μm, 5 μm, 3.2 μm, 1 μm, 0.4 μm, 0.2 μm or 0.1 μm can be selected. As an alternative, ion exchangers or sorbents with attached ligands are possible.

The barrier and the opener are arranged preferably in such a way that the opener is arranged closer to the second chamber than the barrier. The barrier can protect the opener from the ingress of body fluid. The barrier can also prevent fluid from escaping from the first chamber. The filter can be arranged between the barrier and the opener. The opener can open a closure of the second chamber. The barrier, in particular, in the form of the aforementioned check valve or umbrella valve, can be opened, in particular, in the event of a longitudinally axial displacement; and the opener can open the second chamber in the event of this longitudinally axial displacement. In this way a connection can be established between the first and the second chamber, for which connection at least two closures or exactly two closures (on the one hand, the barrier and, on the other hand, the closure of the second chamber) are used in order to ensure sterility to the greatest extent possible.

In a preferred embodiment the second chamber has a negative pressure, as a result of which the transfer of at least part of the body fluid between the first and the second chamber can be simplified. A simple design of a second chamber of a constant effective size is possible. There is no need for the walls of the chamber to move in relation to one another, so that said movement would effect a change in the effective size of the chamber. As an alternative or in addition, it can be provided that an air outlet is provided on the second chamber, where said air outlet can be designed to balance the pressure in the second chamber. It is particularly preferred that the air outlet may be designed in the manner of a check valve, in which a closing element is positively closed in one direction and releases a flow of air in the other direction. For example, such a check valve can have a spring that closes the closing element in one direction by means of the spring and that in the other direction releases the flow of air from the chamber to the outside. Closing elements that may be considered include a cone, ball, flap and/or diaphragm, which in each case is pressed into a corresponding seat. If there is pressure in the direction, in which the closing element releases a flow that exceeds the force of the spring, then the closing element is lifted off the seat; and the throughflow is free. Embodiments, in which no spring is used, are also possible, for example, an embodiment, in which the closing element closes primarily only due to a higher external pressure of a fluid, the flowing air or the weight of the closing element.

The second chamber is displaceable preferably with respect to the first chamber, in particular, along the longitudinal axis of the first chamber. The second chamber can be arranged so as to be preferably displaceable on or in a guide. A blocking means can be provided that prevents the second chamber from moving in relation to the first chamber. The blocking means can be designed as a stop element that can be removed in order to release the blocking or can be brought into a different position in relation to a support element. In a preferred embodiment the blocking can be released automatically during a centrifugation run of the apparatus. In an alternative, particularly preferred embodiment the blocking can be released by the operator prior to the centrifugation run. Suitable blocking means for the purpose of the patent specification include tear tabs or compressible springs. The second chamber can be moved relative to the first chamber preferably in a displaceable manner, wherein the second chamber is able to move towards the first chamber. In addition to the relative movement of the first chamber and second chamber, the second chamber can perform preferably a relative movement in or, more specifically, on the guide. The relative movement between the first chamber and the second chamber can be brought about by a movement of the guide, which can be part of a plunger, by moving the second chamber together with the guide relative to the first chamber. The apparatus can allow multiple relative movements: a) the second chamber and the guide move together relative to the first chamber and b) the second chamber moves relative to the guide. In a particularly preferred embodiment the second chamber can be designed as a container, which can have, in particular, a negative pressure (for example, as a vacuum vial), which is mounted in the guide. The container (second chamber) can be separated from the guide after the body fluid has been transferred to the second chamber. For this purpose the container (optionally together with a support structure) can be pulled out of the guide along the longitudinal axis of the apparatus. Any existing support structure can be removed from the container (second chamber). In order to improve handling, the support structure can have a plunger or handle that extends at the end of the support structure along the longitudinal axis of the apparatus.

It can be provided that the second chamber has a fill opening and a withdrawal opening, which is separate from the fill opening; and said fill opening and withdrawal opening may each have a septum. In this way it can be ensured that the fill opening does not also have to be used as a withdrawal opening, a feature that further reduces the risk of contamination.

In one embodiment the opener and/or an opening on the second chamber can be formed and/or arranged substantially centrally with respect to the cross section of the apparatus. This feature enables a simple configuration. However, it can also be provided that the opener and/or an opening on the second chamber is and/or are formed or arranged so as to be off-centered in relation to the cross section of the apparatus, a feature that can be advantageous in the case of fixed angle rotors.

The term "spring" for the purpose of the patent specification includes a technical component that can be elastically deformed. Non-limiting examples of springs are coil springs, tension springs and bar springs.

In a preferred embodiment the first chamber comprises a cylinder as a cylindrical section and a displaceable guide, which can be moved in the cylinder and which can envelop the displaceable wall. The second chamber can be mounted as a container on the guide in such a way that in the centrifugation process the container is moved relative to the guide in the direction of the first chamber, in order to transfer body fluid from the first chamber to the container. The second chamber can move in the longitudinal direction of the first chamber. The second chamber can have a constant effective size.

The term "guide" for the purpose of the patent specification includes a guide surface that is connected to the displaceable wall. The guide surface can extend substantially parallel to the longitudinal axis of the apparatus. The second chamber can be moved in the longitudinal direction of the apparatus along the guide surface. The guide surface can be designed as a lateral surface of a cylinder, where said lateral surface is formed at least in sections and is aligned concentrically with the lateral surface of the cylindrical section of the first chamber. The guide can receive the second chamber in such a way that said second chamber can be displaceable so as to be able to slide in the direction of the longitudinal axis of the apparatus; and the guide surface can be an inner lateral surface. The second chamber can slide directly or indirectly on the guide. In the indirect case the second chamber can be held in a holder that can slide on the guide surface of the guide. At least one sealing means can be arranged in the circumferential direction between the holder or the second chamber and the guide surface of the guide.

The term "holder" for the purpose of the patent specification includes a technical component that is suitable for receiving the second chamber. For the purpose of the patent specification the holder can be designed as a clamp-like component, which surrounds a second chamber that is designed as a container. The holder can have an opening that is directed in the direction of an opening of the second chamber. The holder can have a substantially cylindrical lateral surface, which is designed at least in sections and which surrounds the second chamber on the circumference thereof at least in sections. Furthermore, the holder can have a base that is designed to bear against an outside of a base of the second chamber. The inside of the lateral surface of the holder can be adapted with respect to its inside diameter to an outside diameter of the second chamber. On the end opposite the base there are provided locking projections, which are adapted to a height of the second chamber, so that the second chamber is held in the holder in the manner of a kind of shape lock. The holder can slide on the guide with its side wall, which is designed at least in sections as a lateral surface of a cylinder. In order to reduce the contact between the guide and the holder, projections, which can slide on the guide surface of the guide surface, can be formed on the holder. In particular, a seal between the guide or, more specifically, the guide surface and the outside of the holder can be formed between the projections.

In a particularly preferred embodiment of the invention the guide can move together with the displaceable wall of the first chamber relative to the first wall—with a change in the size of the first chamber. Furthermore, the holder of the second chamber can move relative to the guide and, in so doing, also relative to the first wall—without a change in the size of the first chamber.

In a preferred embodiment the first chamber has a cylindrical section, designed as a cylinder, and a wall, which is mounted in the cylinder so as to be displaceable. Furthermore, the first chamber has an opening on a connecting part, in particular, with a septum. The connecting part with the opening is designed, in particular, on the outside of a transverse surface of the cylinder, which lies opposite the displaceable wall. The displaceable wall can have a valve that is closed by moving the displaceable wall in order to enlarge the first chamber, especially when the first chamber is being filled, and is opened to transfer the body fluid to the second chamber. The displaceable wall can be connected to a guide. The guide and the displaceable wall can be designed or arranged in the cylinder in such a way that they can be displaced together in the cylinder, wherein the guide is arranged on the side, which is opposite the opening of the first chamber and towards the displaceable wall. Towards the inner surface of the cylinder, in which the displaceable wall is mounted so as to be displaceable, said displaceable wall can have at least one sealing element in the form of an O-ring. The displaceable wall can have, in particular, an opening with a valve. Furthermore, the displaceable wall can also have a selection means, in particular, in the form of a filter, which is arranged between the first chamber and the second chamber. The filter can be permanently connected to the displaceable wall. An opener in the form of a piercing means, in particular, in the form of a cannula, the tip of which is aligned in the direction of the second chamber, can be arranged between the filter and the second wall. The displaceable wall, the filter, the opener and the guide can be designed as part of a plunger, which can be moved so as to be displaceable in the cylinder or, more specifically, the cylindrical section, or can form a part of a displaceable cylinder, which is mounted in a displaceable manner in the cylindrical section or, more specifically, the cylinder. Displaceable wall, filter, opener and guide can be handled as a whole and can be moved in the cylinder or, more specifically, the cylindrical section as a whole. In particular, it is possible to provide an actuating element, which is designed, in particular, as a pressure element on the guide, and which can interact with a barrier, which is designed, in particular, as a valve, on the displaceable wall in such a way that when pressure is applied, for example, by means of the second chamber, the valve opens. When the effect of the barrier is removed, that is to say, when, in particular, pressure is no longer applied to a closure part of the valve, the barrier, in particular, the valve, can open and can bring the two chambers into fluid communication with one another. The barrier or rather the valve can also be designed without an actuating element. The valve can open, for example, due to "excess pressure" applied to the valve. The barrier is opened preferably when the second chamber, which is mounted in or, more specifically, on the guide, has moved towards the guide in such a way that the piercing means has pierced a sealing means that is provided at an opening in the second chamber. The second chamber is designed preferably as a container, in which a negative pressure is present. The second chamber can be mounted in or, more specifically, on the guide in such a way that the second chamber can move towards the piercing means, in order to establish a fluid communication between the first chamber and the second chamber. For this purpose it is possible to provide an embodiment, in which the second chamber is moved towards the piercing means, in order to pierce the sealing means of the second chamber; and in an additional movement or in the same movement the second chamber presses directly or indirectly a pressure means, which opens the valve that is formed on the displaceable wall. The valve can also be designed in such a way that it opens when there is excess pressure in the first chamber. The valve can also be designed as a check valve. The second chamber can be moved preferably together with the guide and, thus, together with the displaceable wall, the filter and the piercing means. However, the second chamber can also be mounted additionally in the guide, in order to perform a relative movement with respect to the guide. For this purpose the second chamber can be designed as part of a plunger that can move in a cylindrical section of a guide. The guide, which is part of a plunger in the cylindrical section of the first chamber, can have, in particular, a cylindrical section, in which the second chamber is designed as a plunger. In particular, the second chamber, which is designed as a container, can be sealed off from an inner wall of a cylindrical section of the guide by means of one or more sealing means, which can be designed, in particular, as an O-ring. In particular, it can be provided that a movement of the second chamber within the guide can be prevented by means of a blocking means. After removing the blocking means and/or disengaging the blocking means, a movement of the second chamber relative to the guide can take place. The movement of the guide relative to the cylindrical section or, more specifically, the cylinder of the first chamber and the movement of the second chamber relative to the guide can take place in essence on the same longitudinal axis. Preferably following removal of the blockage of the movement of the second chamber, designed as a container, a displaceable movement of the second chamber relative to the guide can take place; and during said displaceable movement in a first step for connecting the first chamber and the second chamber, the sealing means of the second chamber can be pierced by the piercing means by moving the second chamber relative to the guide; and then in a next step, in which the second chamber is moved together with the guide, the valve is opened. Owing to the forces acting in the centrifugation process, the centrifugation process initiates, in addition to a separation of the phases of the body fluid contained in the first chamber, a movement of the second chamber in the guide, where said movement is substantially transverse to the phase limits, which have been formed, and/or in the direction of the longitudinal axis of the apparatus. As a result of the movement of the second chamber, said second chamber is opened first by the piercing means; and then the valve between the first and the second chamber is opened. Furthermore, the guide moves together with the displaceable wall in the same direction as the second chamber together with said guide, so that a pressure is exerted on the body fluid, located in the first chamber, and the body fluid is pushed out of the chamber and sucked into the second chamber by means of the vacuum. The movement and mounting of the guide in the cylindrical section of the first chamber and the mounting and arrangement of the second chamber in the guide are designed or, more specifically, adapted to each other in such a way that the described relative movements and, in particular, a transfer of a phase, produced during the centrifugation process, to the second chamber take place. After the centrifugation process for separating the phases, the apparatus can be removed from the centrifuge; and then the second chamber can be removed from the guide, wherein a movement is carried out that is in the opposite direction of the movement that led to the piercing of the sealing means; and, in so doing, the sealing means is closed again. The second chamber can be handled in any desired way.

The invention also provides a method, in which body fluid is transferred from a first chamber to a second chamber, wherein the effective size of the first chamber is changed by means of a displaceable wall, and the second chamber is moved relative to the displaceable wall. In particular, the first and the second chamber can be connected during a centrifugation run; and the body fluid can be transferred from the first chamber to the second chamber during the centrifugation process by means of the forces acting in the process.

It can be provided that at least part of the body fluid is transferred by displacing the second chamber in the direction of the first chamber. During the displacement it is possible to balance the pressure. As an alternative or in addition, it is possible for the displacement to take place without balancing the pressure. In the case of a displacement without balancing the pressure, there is no need to provide means that have to be used to balance the pressure; the apparatus and/or the number of components can be simplified by the structural configuration. In the case of a displacement with pressure equalization, the displacement process is perhaps easier to carry out, because there is no increased pressure in the sliding direction.

The term "centrifugation" for the purpose of the patent specification includes the process of centrifuging a liquid in a centrifuge, which is commonly referred to as a fixed angle or swing out centrifuge. For example, the apparatus can be placed in centrifuges for 50 ml Falcon tubes. The duration of the centrifugation run can be varied between 1 to 90 minutes and preferably between 1 to 60 minutes. It can be provided that the body fluid is incubated before the centrifugation run or during the centrifugation run, where preferably a longer duration of the centrifugation run is possible in the case of an incubation during the centrifugation process—possibly at lower rotational speeds. Suitable relative centrifugal accelerations (RCA), at which the method can be carried out, are in the range of from 10 to 10,000 G, preferably 10 to 5,000 G, in particular, preferably 10 to 4,000 G. After the centrifugation run, the phase of the body fluid that was originally introduced in the second chamber can be used immediately. As an alternative, the body fluid phase can be cooled, frozen and/or lyophilized or otherwise processed in the second chamber. For the purpose of the patent specification, "any other processing" includes adding additives, portioning into capsules, coating apparatuses to be implanted with the body fluid of the second chamber and other possible uses. One embodiment of a process sequence is described below.

In a preferred embodiment the first chamber can be filled with blood by moving a displaceable wall of the first chamber. The blood is collected preferably directly from an organism with the apparatus comprising the first chamber. In a particularly preferred embodiment the first chamber is filled with 1 to 25 ml, preferably 5 to 20 ml and, in particular, preferably 10 to 15 ml of blood. Then a first incubation of the apparatus, filled with blood, can be carried out, followed by centrifugation. As an alternative, the apparatus, which is filled with blood, can also be centrifuged immediately after having been filled, wherein an incubation can be carried out while centrifuging.

The term "incubation" for the purpose of the patent specification includes a defined interim storage or storage of the apparatus under defined conditions, which are primarily the temperature and the time. Interim storage or storage can also take place inside the centrifuge.

The duration of an incubation can be varied, just like the temperature. Structures, which change and/or enlarge the inner surface area, are provided preferably in the first chamber and can have an inducing effect on the formation of autologous proteins. A non-limiting example of the enhanced formation of autologous proteins is the interleukin 1 receptor antagonist (IL-1 Ra). Conditions suitable for incubation for the enhanced formation of IL-1 Ra are known to the person skilled in the art, inter alia, from the document EP 1 151 004 B1. Some examples that can be mentioned include an incubation period for 24 hours at 37 to 41° C. and an incubation period for 12 to 72 hours at room temperature. In the example an incubation period can be followed by a centrifugation process for the separation of individual blood constituents. In this case the method relates to a centrifugation process, in which a blood phase is transferred to a first chamber during the centrifugation run. The transferred blood phase is preferably blood plasma or blood serum. In a particularly preferred embodiment the blood phase to be transferred is enriched with autologous IL-1 Ra.

The invention also provides a use of forces, which act during a centrifugation run and which are used to separate the phases of a body fluid, wherein the forces are also used to connect a first chamber and a second chamber and to transfer the body fluid from the first chamber to the second chamber.

In addition to the specified numerical values, numerical data also include, in particular, tolerance-related deviations of +/−20%, in particular, preferably +/−10%, and, thus, a corresponding range of values.

The explanations in the patent specification regarding the aspects of the apparatus, the method and the use complement one another, so that explanations regarding one aspect of the invention also apply to the other aspect of the invention.

The invention is explained in more detail below with reference to one exemplary embodiment shown in the drawings.

The foregoing explanations as well as the following description of exemplary embodiments do not constitute a waiver of certain embodiments or features.

Figure 4:
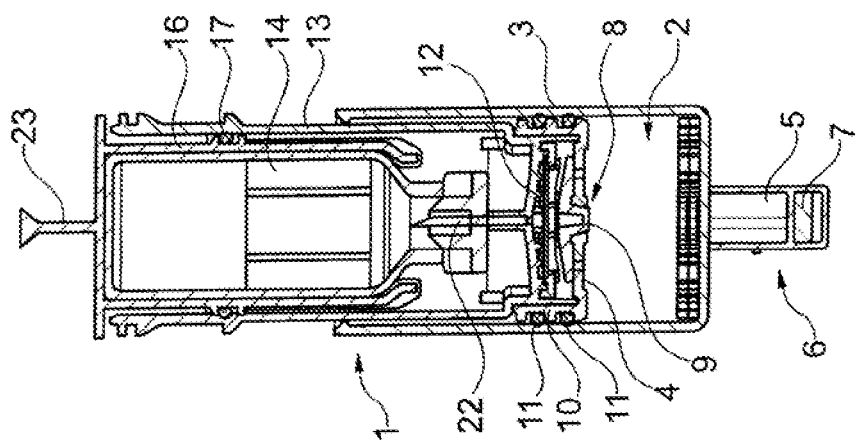
Figure 3:
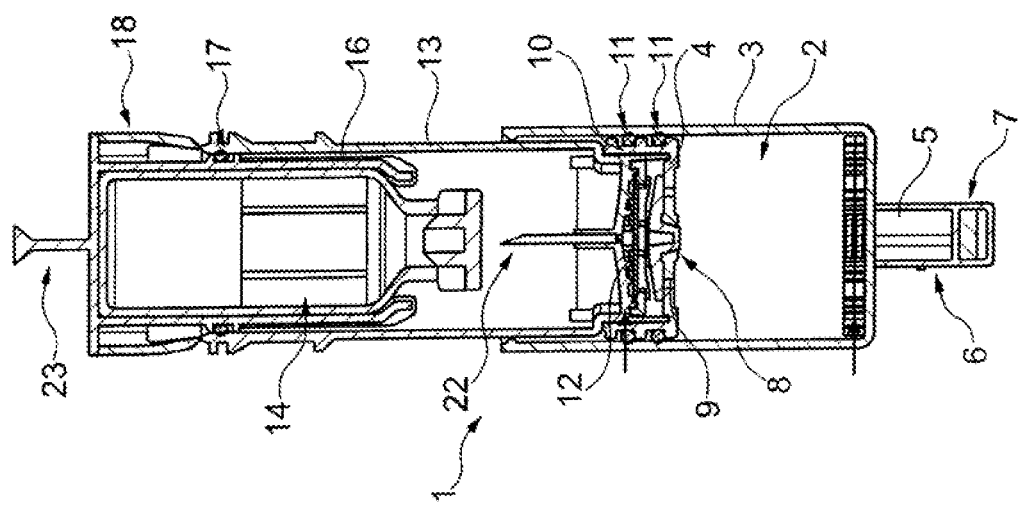
Figure 2:
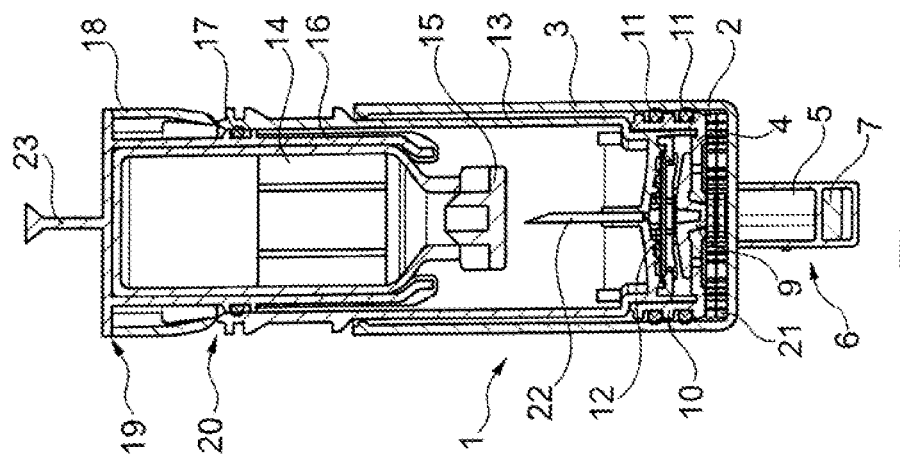

The drawings show in:

FIG. 1: an apparatus in an isometric view obliquely from above;

FIG. 2: the apparatus from FIG. 1 in a basic position in a partially sectioned illustration;

FIG. 3: the apparatus from FIG. 2 after having been filled;

FIG. 4: the apparatus from FIG. 3 after a centrifugation run; and

Figure 5:
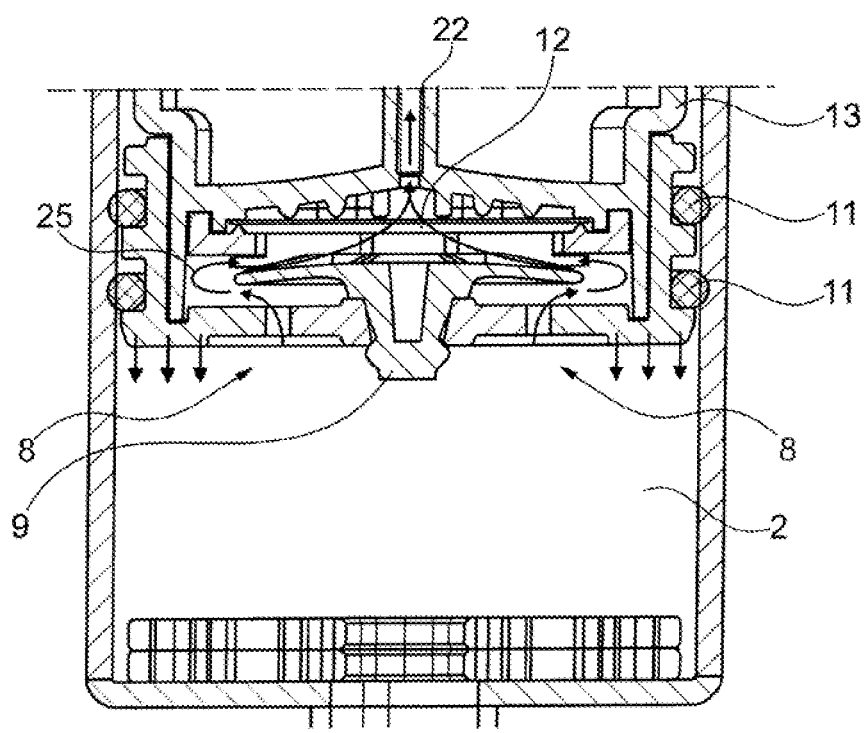

FIG. 5: a detailed view of the apparatus.

FIG. 1 shows an isometric view of an apparatus 1, which is described in more detail with reference to the following figures.

FIG. 2 shows a schematic representation of the apparatus 1 in a partially sectioned illustration. The apparatus 1 is in a first state, which corresponds to a basic position upon delivery of the apparatus 1 and the representation in FIG. 1.

The apparatus 1 comprises a first chamber 2, which has a variable effective volume. The first chamber 2 has a cylindrical section or, more specifically, a cylinder 3, in which a wall 4 is mounted in a displaceable manner. In the exemplary embodiment shown in FIG. 1, the cylinder 3 is a circular cylinder; and the wall 4 is a circular area that is adapted to the internal dimensions of the cylinder 3. The wall 4 is displaceable along a longitudinal axis of the cylinder 3. The chamber 2 has an opening 5 that is formed on a transverse surface of the cylinder 3. A connecting part 6 is provided in the area of the opening 5 and is designed to be connected to an external element, such as a cannula or needle. In the area of the opening 5 there is a septum 7, with which a connection to the first chamber 2 can be reversibly established and closed again. The first chamber 2 can be filled with body fluid by means of the external element and the opening 5.

The wall 4 has at least one opening 8, in the illustrated case a plurality of openings 8, which can be either closed or opened by means of a barrier 9 that is designed as a valve (an umbrella valve). Furthermore, the wall 4 also has a section 10, which extends in the direction of the displacement (longitudinal axis) and on which seals 11 are provided that seal the first chamber 2 when it moves with respect to the wall 4. The seals 11 are designed in the form of O-rings that extend in the circumferential direction around the longitudinal axis. The seals 11 are arranged in receptacles of the section 10. The seals 11 produce a seal between the wall and the cylinder 3.

Connected to the wall 4 is a selection means 12 that is designed as a filter and together with the barrier 9, which is designed as a valve, can be displaced in the longitudinal direction of the cylinder 3. The wall 4 is connected to a guide 13, which in turn is designed as a cylindrical element in the case, shown in the exemplary embodiment, and extends away from the wall 4.

A second chamber 14 is arranged on the guide 13 and can be displaced in the guide 13 in the longitudinal axis of the cylinder 3 and the guide 13. The second chamber 14 is designed as a container that has a negative pressure. The second chamber has a constant effective size. The second chamber 14 is closed by means of a sealing means 15. The second chamber 14 is held in the guide 13 by a holder 16 that has an outer dimension that is adapted to the inner dimensions of the guide 13. The holder 16 can be displaced in the guide 13 by sliding. In order to seal towards the outside, the holder 16 has an O-ring 17 that is disposed in a circumferential groove around the holder 16.

In the state shown in FIGS. 1 to 3, a blocking means 18, which is designed as a tear tab, is provided between the guide 13 and holder 16, in order to prevent a relative movement along the longitudinal axis of the apparatus 1 between the holder 16 and, thus, the second chamber 14 relative to the guide 13. The blocking means 18 is arranged between a stop section 19 of the holder 16 and an end-sided section of the guide 13, with said stop section extending in the transverse direction of the longitudinal axis.

FIG. 3 shows the state of the apparatus 1 from FIGS. 1 and 2, respectively, in a state after having been filled with body fluid, in this case with blood. The apparatus 1, in this case the first chamber 2, is filled by connecting the connecting part 6 to a cannula and by moving the wall 4, in order to increase the effective size of the first chamber 2, while one end of the cannula is stuck into a lumen of a human or animal body filled with blood. The body fluid is drawn into the first chamber 2. The wall 4 is moved by gripping a grip section 24, which is formed on the guide 13 transversely to the longitudinal axis of the apparatus 1, and then pulling the wall 4 towards the rear along the longitudinal axis. The grip section 24 is delimited by projections 24a, 24b that are spaced apart in the longitudinal direction. The projections 24a, 24b extend around the guide 13 along the circumference. When filling with body fluid, the barrier 9, which is designed as an umbrella valve, is closed, so that the first chamber 2 receives the body fluid; and, when the cannula is separated again from the connecting part 6, the body fluid in the first chamber 2 is sterile. For a sterile incubation, a substance 21, which enlarges or rather changes the inner surface area, is provided in the first chamber 2 and can have an inducing effect on the formation of autologous proteins.

Centrifugation can be performed after or during the sterile incubation. The resulting state of the apparatus 1 is shown in FIG. 4. The blocking means 18 was removed prior to the centrifugation process.

FIG. 4 shows the state of the apparatus 1 after the centrifugation process, during which process, on the one hand, the body fluid, in this case the blood, was separated into the individual phases; and a movement of the guide 13, the wall 4 and the second chamber 14 was induced due to the forces generated during the centrifugation process. As a result, the body fluid can be separated into individual phases; and, in particular, one of the phases can be transferred to the second chamber 14 during the centrifugation process. By removing the blocking means 18 it is possible for a movement of the second chamber 14 or, more specifically, the holder 16 for the second chamber 14 relative to the guide 13 to take place, so that the holder 16 together with the second chamber 14 moves along the longitudinal axis of the guide 13 or, more specifically, towards the first chamber 2, while the sealing means 15 of the second chamber 14 is pierced by an opener 22, which is designed as a piercing means; and, in so doing, the second chamber 14 is opened. Thus, the second chamber 14 is in fluid communication with the filter 12 and the valve 9.

By lowering the holder 16 and the second chamber 14 it is possible to apply pressure to the barrier 9, so that the barrier 9, which is designed as a valve, opens the openings 8 of the first chamber 2; and, in so doing, the first chamber 2 and the second chamber 14 are connected to each other. Owing to the forces acting during the centrifugation process, the guide 13 together with the second chamber 14 and the wall 4 is displaced in the direction of the opening 5, so that during the movement caused by the centrifugal forces, the top phase of the phases that are separated from the body fluid is transferred. This state is shown for the end of the transfer in FIG. 4.

After centrifuging, the container in the form of the second chamber 14 can be removed from the guide 13. For this purpose an operator can grip the apparatus 1 by a grip 23, which is formed on the end of the holder 16, and can take said apparatus out of the centrifuge. Then the apparatus 1 can be held on one side of the grip section 24; and the holder 16 can be pulled out of the guide 13. In the course of removing by means of a longitudinally axial movement of the holder 16 with the chamber 14 away from the opener 22, the sealing means 15 of the second chamber 14 is closed again.

The container in the form of the second chamber 14 can be removed from the holder 16. The separated phase, located in the second chamber 14, was processed in a sterile manner and transferred sterile from the first chamber 2 to the second chamber 14 without the need for a process step performed by an operator.

FIG. 5 shows a detailed view of the apparatus 1. The curved arrows 25 indicate in schematic form a fluid path that is produced when the barrier 9 is opened. The barrier 9, which is designed as an umbrella valve, opens the openings 8 in the wall 4. The opening of the openings 8 is mainly due to the pressure that is generated by the body fluid and is caused by the displacement of the wall 4 in the direction of the opening 5. The displacement of the wall 4 is indicated by the three arrows on the right and left. Fluid flows from the first chamber 2 through the openings 8, through the selection means 12, and further through the opener 22 into the second chamber 14.

The invention claimed is:

1. An apparatus for receiving a body fluid, wherein the apparatus comprises:
   a) a first chamber that can receive the body fluid, the first chamber having a cylindrical section, designed as a cylinder, and a displaceable wall, the first chamber further having an opening on a connecting part, which lies opposite the displaceable wall, the connecting part being designed to be connected to an external element, the displaceable wall having an opening, which can be selectively opened or closed by means of a barrier, wherein the displaceable wall is connected to a guide, the guide and the displaceable wall being arranged in the cylinder in such a way that the guide and the displaceable wall can be displaced together in the cylinder, wherein the guide is arranged on the side which is opposite the opening of the first chamber, and b) a second chamber which is mounted in or on the guide and that can receive the body fluid, the second chamber being closed by a sealing means, the second chamber having a constant effective size, wherein the size of the first chamber can be increased in order to draw the body fluid into the first chamber by moving the displaceable wall, wherein a movement of the second chamber within the guide is prevented by means of a blocking means, which can be removed, and after removing the blocking means, a movement of the second chamber relative to the guide and the displaceable wall can take place, the apparatus is designed to connect the first chamber and the second chamber to transfer body fluid from the first chamber to the second chamber via a longitudinally axial movement of the second chamber with respect to the displaceable wall in a first step, in which the sealing means of the second chamber is pierced by an opener, and in a next step, in which the second chamber moves together with the displaceable wall, the opening of the first chamber in the displaceable wall is opened.

2. The apparatus as claimed in claim 1, wherein the two chambers are closed to the environment after receiving the body fluid.

3. The apparatus as claimed in claim 1, wherein the barrier is designed as a check valve or "duckbill valve" or as an umbrella valve, which is arranged on the outside of a wall of the first chamber.

4. The apparatus as claimed in claim 1, wherein the opener is arranged between the first and second chamber.

5. The apparatus as claimed in claim 1, wherein a selection means which is designed as a filter is arranged between the first and second chamber.

6. The apparatus as claimed in claim 1, wherein a septum is provided for reclosing the first chamber after filling.

7. The apparatus as claimed in claim 1, wherein a substance, enlarging the inner surface area of the first chamber, is arranged in the first chamber, the substance having an inducing effect on the formation of autologous proteins.

8. The apparatus as claimed in claim 1, wherein the second chamber has a negative pressure or an air outlet.

9. The apparatus as claimed in claim 1, wherein the movement of the displaceable wall is limited by means of a stop element.

10. The apparatus as claimed in claim 1, wherein the apparatus can be filled in a sterile manner.

11. The apparatus as claimed in claim 1, wherein the first chamber comprises a biologically active substance.

\* \* \* \* \*